United States Patent [19]

Weisrock et al.

[11] 4,407,951

[45] Oct. 4, 1983

[54] *XANTHOMONAS CAMPESTRIS* ATCC 31600 AND PROCESS FOR USE

[75] Inventors: William P. Weisrock, Tulsa, Okla.; Edward F. McCarthy, Naperville, Ill.

[73] Assignee: Standard Oil Company (Indiana), Chicago, Ill.

[21] Appl. No.: 167,871

[22] Filed: Jul. 14, 1980

[51] Int. Cl.[3] ........................ C12P 19/06; C12N 1/20; C12R 1/64

[52] U.S. Cl. .................................... 435/104; 435/253; 435/910

[58] Field of Search ........................ 435/104, 253, 910

[56] References Cited

FOREIGN PATENT DOCUMENTS 1512536 6/1978 United Kingdom ................ 435/104

OTHER PUBLICATIONS

Gaby et al., Journal of Bacteriology, vol. 74, pp. 356–358 (1957).
Gibbs et al., Identification Methods for Microbiologist, vol. A, 1966, pp. 9–14.
Hayward et al., Journal General Microbiol, vol. 26, pp. 133–140 (1961).
Christensen, Jour. Bacteriology, vol. 52, pp. 461–466 (1946).
Ivanoff et al., Jour. Bacteriology, vol. 35, pp. 235–253 (1938).

*Primary Examiner*—Lionel M. Shapiro
*Attorney, Agent, or Firm*—Stephen R. May; Fred E. Hook

[57] ABSTRACT

A new degenerative-resistant strain of *Xanthomonas campestris* is described which is suitable for longterm continuous fermentation to produce xanthan gum from a nutrient medium, typically containing inorganic salts, glucose, $NH_4Cl$, and citric acid, with or without yeast extract or yeast autolysate.

14 Claims, No Drawings

XANTHOMONAS CAMPESTRIS ATCC 31600 AND PROCESS FOR USE

INTRODUCTION

The present invention relates to the production of heteropolysaccharides by the action of certain novel degenerative resistant strains of *Xanthomonas campestris* on minimal media. More particularly, it is concerned with the production of xanthan gum by the use of these novel bacteria on aqueous nutrient media having assimilable sources of carbon, nitrogen and inorganic substances.

BACKGROUND

Batch fermentation of inoculated medium with *Xanthomonas campestris* NRRL B-1459 for 36-72 hours under aerobic conditions results in the formation of xanthan gum, which is separated from the other components of the medium by precipitation with acetone or methanol in a known manner. Because of time required to ferment each batch, the low biopolymer content of the fermented medium and the processing required for the recovery and purification of the product, xanthan gum produced by batch fermentation, hereinafter also referred to as xanthan, is relatively expensive.

Because continuous operation of a fermentation process offers a number of potential advantages over conventional batch methods that could be reflected in lower costs, considerable effort has been put forth in the past to perfect conditions that would support a reliable continuous process. But even with a continuous process a cheap medium from which xanthan can be produced is required. In addition to the necessity of an inexpensive medium in the manufacture of a low cost xanthan product, the ratio of xanthan to cells (bacteria) should be as high as possible in order to reduce subsequent filtration costs for cell removal. The specific productivity of the culture employed also should be as high as possible in order to maintain the aforesaid high ratio as well as to reduce vessel volume and capital costs. The expression "specific productivity" as used in the present description is intended to mean the number of grams of xanthan produced/grams of cells/hour. The culture should be stable under continuous culture conditions on a long term basis to avoid frequent restarts and lost productivity.

Although xanthan has been produced by continuous fermentation in the past, such methods have not met with unqualified success. In some cases, vitamins and/or amino acids had to be employed in the media in substantial quantities in order to avoid culture degeneration or to improve specific productivity. Use of these additives, as well as soybean protein, cotton seed protein, etc., all tend to make the xanthan thus produced more costly.

It is well known that the continuous production of xanthan has been hampered by a tendency of the culture *Xanthomonas campestris* B-1459 to change or degenerate after a fairly small and specific number of turnovers, i.e., the time required during the fermentation to completely replace one volume of broth in the fermentation vessel. Normally, 6-9 turnovers are the maximum that can be obtained before degeneration of the culture occurs. At the same time, there is a decrease in viscosity, a loss in volumetric productivity of xanthan, i.e., grams of xanthan/liter of broth/hour, and appearance of a variety of culture variants or strains that no longer produce xanthan or else produce a xanthan of low quality. It has been demonstrated, for example, that culture degeneration occurs when dried distillers solubles (DDS) is used in the medium as the complex nitrogen source, whether in the whole form or as a water soluble extract. In other cases, certain strains of Xanthomonas have been grown successfully without culture degeneration in simple minimal media, but the xanthan:cell ratio and specific productivity have been low, on the order of 0.1-0.12 gm xanthan/gm cells/hr.

Earlier work has indicated that heteropolysaccharides produced by the action of Xanthomonas bacteria on carbohydrate media have potential applications as film forming agents, as thickeners for body building agents in edible products, cosmetic preparations, pharmaceutical vehicles, oil field drilling fluids, fracturing liquids and similar compositions and as emulsifying, stabilizing and sizing agents. Heteropolysaccharides, particularly xanthan gum, have significant potential as a mobility control agent in micellar polymer flooding. This gum has excellent viscosifying properties at low concentration, is resistant to shear degradation and exhibits only minimal losses in viscosity as a function of temperature, pH and ionic strength. For these reasons, xanthan gum is an attractive alternative to synthetic polyacrylamides for enhanced oil recovery operations.

SUMMARY OF THE INVENTION

We have now discovered a degenerative-resistant strain of *Xanthomonas campestris* and have developed a process for using this strain which effectively overcomes the problems of xanthan production recited above. This strain of *Xanthomonas campestris* which we have designated *Xanthomonas campestris* XCP-1 ATCC 31600 is capable of continuously producing xanthan at high specific productivities, i.e., 0.24 to 0.32 gm xanthan/gm cells/hr, for several hundred hours without culture degeneration from inexpensive aqueous nutrient media such as, for example, minimal medium consisting primarily of inorganic salts, glucose and $NH_4Cl$. The medium may or may not also contain a yeast extract or yeast autolysate as a supplemental nitrogen source. Generally, it may be said that any medium having assimilable sources of carbon, nitrogen and inorganic substances will serve satisfactorily for use with this new organism.

The process of our invention in which this new strain is utilized can be either a single stage or two-stage continuous fermentation process. In the single stage embodiment the organism is grown, preferably under conditions such that the quantity of one of the growth nutrients present is limited. The quantity of biomass obtained will be determined by the concentration of the limiting nutrient. A portion of the residual glucose or equivalent sugar present is converted to xanthan gum and the latter ultimately recovered from the fermentation effluent. In the two-stage process, the aforesaid fermenter effluent is taken to a second fermentation stage where additional glucose or equivalent sugar is introduced and converted to xanthan. In operation of the second stage, a balance of the flow of the first stage effluent and glucose solution must approximate the flow rate of the second stage effluent. The growth limiting nutrients normally employed are nitrogen, phosphorous or sulfur.

SPECIFIC EMBODIMENTS OF THE INVENTION

Subcultures of this living organism can be obtained upon request from the permanent collection of the American Type Culture Collection, 12301 Parklawn Drive, Rockville, MD 20852. The accession number in this repository for *Xanthomonas campestris* XCP-1 is given above. The novel *Xanthomonas campestris* strain referred to was isolated from a pilot plant run in which a 28 liter fermenter was operated using a culture of *Xanthomonas campestris* NRRL B1459, growing in a suitable nutrient medium having a composition shown in Table I.

TABLE I

| Component | Concentration (ppm) |
|---|---|
| Glucose | 22,000 |
| $NH_4Cl$ | 300 as N |
| KOH | 1000 + as K |
| $H_3PO_4$ | 300 as P |
| $MgSO_4$ | 100 as Mg |
| $CaCl_2$ | 10 as Ca |
| NaCl | 10 as Na |
| $FeSO_4$ | 2 as Fe |
| $ZnSO_4$ | 0.35 as Zn |
| $MnSO_4$ | 0.35 as Mn |
| $Na_2MoO_4$ | 0.21 as Mo |
| $H_3BO_3$ | 0.07 as B |
| KI | 0.14 as I |
| $CuSO_4$ | 0.020 as Cu |
| Citric Acid | 250 |

Continuous fermentation of the above medium was initially conducted at 28° C., a pH of 6.8, an aeration rate of 0.2–0.4 vol./vol./min., agitation rate of 230 rpm, dissolved oxygen of 90% saturation, and a dilution rate of 0.08 $hr^{-1}$. After about 6 turnovers, the culture began to degenerate with lowered xanthan productivity and viscosity. At this point, several changes were made to the medium. The pH was lowered to 6.4 from 6.8; iron, copper and zinc concentrations in the broth were raised to 3, 0.6 and 1 ppm, respectively, by adding these trace elements to the glucose feed tank (they were previously added with the rest of the inorganic salts), the citric acid level was doubled to 500 ppm, and $H_3PO_4$ and $MgSO_4$ levels were reduced by half. For 2 to 3 culture turnovers after these changes the culture continued to degenerate with viscosity dropping to 70 cp and specific productivity decreasing to 0.7 gm/gm cells/hr.

During an overnight period, the exit line, from the fermenter plugged and the culture went into a semi-batch/low dilution rate condition for about 10 hours. The following morning, viscosity was up to 300 cp and when level and flow rates were corrected, it continued to increase. For the next 10 turnovers, specific productivity gradually increased to over 0.35 gram of xanthan/gram cells/hour, and culture morphology became normal again. The culture was maintained at this high productivity for some 30 turnovers after recovery without any evidence of culture degeneration before being terminated by a pH upset. This highly productive culture was saved in a viable state and used to isolate the novel *Xanthomonas campestris* strain referred to above.

After standard plate counts were made on the culture, using YM agar (Difco), 9 isolated colonies of varying sizes were picked and subcultured on YM agar for purification. Three isolates were discarded as obvious duplicates, and the remaining six isolates were maintained for three bi-weekly transfers on YM agar slants. The isolates were then subcultured to EMSY-1 broth and then maintained on EMSY-1 agar slants as well as on the YM agar slants. In addition, cultures grown in EMSY-1 broth were frozen in liquid nitrogen. The composition of this (EMSY-1) broth is given in Table II.

TABLE II

| Component | Concentration (ppm) |
|---|---|
| Glucose | 10,000 |
| $NH_4Cl$ | 112 as N |
| $KH_2PO_4$ | 386 as P |
| $Na_2HPO_4$ | 390 as P |
| $MgSO_4.7H_2O$ | 40 as Mg |
| $CaCl_2.2H_2O$ | 10 as Ca |
| NaCl | 10 as Na |
| $FeCl.6H_2O$ | 1 as Fe |
| $ZnSO_4.7H_2O$ | 0.33 as Zn |
| $MnSO_4.H_2O$ | 0.1 as Mn |
| $Na_2MoO_4.2H_2O$ | 0.067 as Mo |
| $H_3BO_3$ | 0.033 as B |
| KI | 0.033 as I |
| $CuSO_4.5H_2O$ | 0.2 as Cu |
| Citric Acid | 500 |
| Yeast Extract | 400 |

The *Xanthomonas campestris* XCP-1 strain was obtained by pooling five of the six remaining isolates, i.e., P-101, P-102, P-104, P-105, and P-108, into one culture.

STRAIN DESCRIPTIONS

The above-mentioned strain of *Xanthomonas campestris* was characterized with respect to *Xanthomonas campestris* strain NRRL B-1459 from which it was originally derived. The following descriptions characterize the new strain:

I. Cell Morphology

1. After growth in EMSY-1 broth (composition in Table II) for 18 hours at 28° C., cells appear singly and in pairs, with some chain formation apparent. Cell dimensions are 0.5–1.0 microns in width by 0.7 to 2 microns in length. Chains of 5 to 30 microns in length may be formed.

2. After growth in YM broth (Difco) for 18 hours at 28° C., cells appear singly and in pairs, with frequent chain formation apparent. Cells are larger than in the minimal medium described above and have the dimensions of 0.75–1.2 microns in width by 1–4 microns in length. Chains of 5–40 microns in length are found.

3. Strain XCP-1 does not exhibit motility, has a negative Gram stain reaction, and does not form endospores. These bacteria may be reproduced only asexually by means of binary fission.

II. Colony Morphology

1. After 72 hours growth at 28° C. on EMSY-1 agar plates (composition in Table II) isolated colonies are yellow, circular, entire, mucoid, raised, and with a translucent periphery. Colony diameter is 2–3 mm. Colonies exhibit color variations in that both light yellow and darker yellow colonies are present. This color variation is a stable property of the culture in that single isolated colonies of either color will give rise to a mixture upon subculture.

2. After 72 hours growth on YM agar (Difco) plates at 28° C., isolated colonies are yellow, circular, entire, mucoid, and raised. Colony diameter varies from 1.5 to 4 mm. Colonies are slightly darker yellow than on EMSY-1 agar, but the variable color (light and dark yellow) is also present.

3. After 72 hours growth at 28° C. on Nutrient Agar (Difco) plates containing 1% dextrose, isolated colonies are circular, entire, mucoid, and raised. Colony diameter is 0.5-1.5 mm. Color variation is also present and is of three types: (a) pale yellow to cream, (b) light yellow, and (c) dark yellow.

III. Biochemical Characteristics

In order to determine whether strain XCP-1 is physiologically different from *Xanthomonas campestris* NRRL B-1459, the following tests were conducted.

1. Growth at 35° C. Inoculated slants of YM agar (Difco) and EMSY-1 agar (see Table II for composition) were incubated at 35° C. for five days and results are given in Table III.

TABLE III*

| Strain No. | YM Agar | EMSY-1 Agar |
|---|---|---|
| XCP-1 | 2+ | 0 |
| B-1459 | 2+ | 0 |

*0 = no growth;
1+ = slight growth;
4+ = heavy growth

2. Growth Characteristics in Minimal Medium. Inoculated tubes of liquid EMS-2 medium (glucose, mineral salts, $NH_4Cl$; see Example III for composition) were incubated at 28° C. for 96 hours. Strain XCP-1 showed heavy growth throughout the tubes with a ragged surface pellicle and clumping in the broth. Strain B-1459 showed less growth overall and only a slight surface growth.

3. Hydrolysis of Gelatin, Casein, and Starch. Solid agar media individually containing 0.4% gelatin, 0.4% casein, or 0.3% soluble starch were prepared and used according to the procedure in "Identification Methods for Microbiologists", 1966, B. M. Gibbs and F. A. Skinner, eds., Academic Press, p. 12.

TABLE IV

| Strain No. | Gelatin | Casein | Starch |
|---|---|---|---|
| XCP-1 | 4+ | 4+ | 4+ |
| B-1459 | 4+ | 4+ | 4+ |

Strains B-1459 and XCP-1 showed complete hydrolysis of all three substrates as shown in Table IV.

4. Action on Litmus Milk. Cultures inoculated into Litmus Milk medium (Difco) were incubated at 28° C. for three weeks, according to the method of Ivanoff et al. (1938, J. Bacteriol, 35 235). Strains XCP-1 and B-1459 were both active in litmus milk with peptonization, litmus reduction, and precipitate formation.

5. Hydrogen Sulfide Production. The medium for $H_2S$ production was prepared according to the method of Hayward and Hotchkiss (1961, J. Gen. Microbiol. 26, 133-140). $H_2S$ production was determined by the use of lead acetate paper strips suspended over the medium in loosely capped tubes. The cultures were incubated for six days at 28° C. and observed for blackening of the strips. Each of the strains produced hydrogen sulfide.

6. Urease Production. Urea medium was prepared according to the method of Christensen (1946, J. Bacteriol. 52 461-466). The slants were inoculated and incubated at 28° C. for 14 days. A red to violet color in the medium would be indicative of urea hydrolysis. Urease production was found to be negative for each of the strains tested.

7. Growth in Presence of Salt. Basal media containing NaCl at concentrations of 1, 2, 3, 4, and 5% were prepared according to the method of Hayward and Hotchkiss (1961. J. Gen. Microbiol. 26 133-140). Cultures were inoculated and incubated at 28° C. for 14 days. Both strains tested gave an identical growth pattern as shown in Table V.

TABLE V

| Strain No. | Salt Conc'n | | | | |
|---|---|---|---|---|---|
| | 1% | 2% | 3% | 4% | 5% |
| XCP-1 | 4+ | 3+ | 3+ | 2+ | 0 |
| B-1459 | 4+ | 3+ | 3+ | 2+ | 0 |

8. Carbohydrate Assimilation Pattern. A basal carbohydrate assimilation medium was prepared according to the method of Hayward and Hotchkiss (1961. J. Gen. Microbiol. 26 133-140). Each strain was inoculated into replicate tubes containing the carbohydrates shown in Table VI, and incubated for 14 days at 28° C.

TABLE VI

| Carbohydrate | XCP-1 | B-1459 |
|---|---|---|
| Glucose | + | + |
| Galactose | + | + |
| Arabinose | + | + |
| Mannose | + | + |
| Melibiose | + | + |
| Cellobiose | + | + |
| Sucrose | weak | weak |
| Fructose | weak | weak |
| Trehalose | + | + |
| Xylose | − | − |
| Mannitol | + | + |
| Lactose | − | − |
| Maltose | + | + |

As can be seen in Table VI, each strain gave an identical assimilation profile.

9. Oxidase Production. Using isolated colonies from 72 hour old YM agar (Difco) plates, the strains were tested for presence of indophenol oxidase using the method of Gaby and Hadley (1957. J. Bacteriol. 74 356-358). Each strain was positive for oxidase.

10. Catalase Production. Growth from a 48 hour YM agar (Difco) slant was tested for catalase activity by emulsifying a loopful of culture in a drop of 3% $H_2O_2$ and observing for effervescence. Strains XCP-1 and B-1459 were both weakly positive.

11. Utilization of Organic Acids. EMS-2 basal medium without glucose (shown in Table VII) was prepared.

TABLE VII

| Component | Concentration (ppm) |
|---|---|
| Glucose | 22,500 |
| $NH_4Cl$ | 224 as N |
| $KH_2PO_4$ | 150 as P |
| $MgSO_4.7H_2O$ | 40 as Mg |
| $CaCl_2.2H_2O$ | 10 as Ca |
| Citric Acid | 500 |
| $FeCl_3.6H_2O$ | 2 as Fe |
| $ZnSO_4.7H_2O$ | 0.66 as Zn |
| $CuSO_4.5H_2O$ | 0.4 as Cu |
| $MnSO_4.H_2O$ | 0.2 as Mn |
| $Na_2MoO_4.2H_2O$ | 0.13 as Mo |
| $H_3BO_3$ | 0.066 as B |
| KI | 0.066 as I |
| NaCl | 10 as Na |

Replicate tubes containing 1% citric, malic, succinic, benzoic, and tartaric acids were inoculated and incubated at 28° C. for 14 days and observed for extent of growth. As shown by the result given in Table VIII, both strains were identical.

TABLE VIII

| Organic Acid | XCP-1 | B-1459 |
|---|---|---|
| Citrate | 3+ | 3+ |
| Malate | 4+ | 4+ |
| Succinate | 4+ | 4+ |
| Benzoate | 0 | 0 |
| Tartrate | 1+ | 1+ |

12. Indole Production. The strains were tested for indole production for the same peptone-water medium used to test for H$_2$S production, following the method of Hayward and Hotchkiss (1961. J. Gen. Microbiol. 26 133–140). All strains were negative for indole production.

13. Acetoin Production. The strains were tested for acetoin production using MRVP medium (Difco) after incubation of the inoculated cultures for six days at 28° C., following the method given in the reference in (12) above. None of the strains tested positive for acetoin.

Summary of Characterization Studies

Strain XCP-1 is essentially indistinguishable from *X. campestris* strain NRRL B-1459 on the basis of cell morphology. However, definite differences in colonial morphology make this strain distinguishable from B-1459. Strain XCP-1 exhibits color variations; i.e., light yellow (larger, 3–4 mm) and darker yellow (smaller, 2–3 mm) colonies on EMSY-1 and YM agar plates, when compared to B-1459. XCP-1 also produces smaller colonies than B-1459 on Nutrient Glucose Agar.

In terms of physiological characteristics, this strain is very similar to NRRL B-1459 except that it grows better on a minimal medium than B-1459.

The foregoing is intended to point out that, while the major distinguishing characteristics of the XCP-1 strain lie in its high xanthan specific productivity and resistance to degeneration in continuous culture, other distinguishing characteristics nevertheless are present.

In carrying out the process of the present invention, the fermenter medium is seeded with an inoculum of culture grown in the same medium as that to be used for fermentation at an inoculum level of 5–10% of the medium volume. The culture is grown in a batch mode for 24–48 hours, until a desired cell concentration is reached (usually 1.5–2.5 gram cells/liter). Thereafter, continuous flow of medium is started into the fermenter such that the dilution rate is 75% or less of the specific growth rate at which the organism is growing at that point. Continuous harvesting of a volume of culture broth equal to the volume of medium introduced is also carried out. After approximately two culture turnovers, the dilution rate is adjusted as desired. Xanthan gum, which exists in the recovered broth, can be used without further purification, or filtered to remove cells, or can be precipitated with an alcohol, such as ethyl or isopropyl alcohol, with or without initial cell removal. The medium used in this process is preferably a minimal medium consisting primarily of inorganic salts, NH$_4$Cl, glucose, and citric acid, with or without additional yeast extract or yeast autolysate.

The term "minimal medium" as used throughout the present description and claims should be interpreted to cover media of the type generally referred to herein and specifically in the Examples, together with modifications apparent to those skilled in this field.

Operating conditions to be employed in the process of our invention include the following:
Agitation: 100–2000 rpm
Preferably: 500–1000 rpm
Air Rate: 0.1–2 vol./vol./min.
Preferably: 0.5–1 vol./vol./min.
Temperature: 20°–35° C.
Preferably: 25°–30° C.
pH: 5–8
Preferably: 6.4–7.4
Dissolved Oxygen: 10–90% saturation
Preferably: 20–60% saturation
Dilution Rate: 0.01–0.15 hr$^{-1}$
Preferably: 0.04–0.1 hr$^{-1}$ Our invention will be illustrated by reference to the following specific examples:

EXAMPLE I

This Example shows that when *Xanthomonas campestris* NRRL B-1459, is grown in a minimal medium in continuous culture, the organism exhibits only low specific productivity and degenerates in a short time. The culture was grown in a 28 liter fermenter in a minimal medium having a composition shown in Table IX.

TABLE IX

| Component | Concentration (ppm) |
|---|---|
| Glucose | 22,000 |
| NH$_4$Cl | 300 as N |
| KOH | 1,000 as K |
| H$_3$PO$_4$ | 150 as P |
| MgSO$_4$ | 40 as Mg |
| CaCl$_2$ | 10 as Ca |
| NaCl | 10 as Na |
| Citric Acid | 500 |
| FeSO$_4$ | 3 as Fe |
| ZnSO$_4$ | 1 as Zn |
| MnSO$_4$ | 0.3 as Mn |
| Na$_2$MoO$_4$ | 0.2 as Mo |
| H$_3$BO$_3$ | 0.1 as B |
| KI | 0.1 as I |
| CuSO$_4$ | 0.6 as Cu |

*Xanthomonas campestris* B-1459 was maintained on YM agar (Difco) slants at 4° C. and transferred to fresh agar slants at bi-weekly intervals. For inoculum preparation, a loopful of culture from a fresh (<3 day old) slant was inoculated into a 16×125 mm tube containing 7 ml of YM broth. The culture was incubated at 28° C. on a rotary shaker at 150 rpm, at a 20° inclination for 18 hours. At this point, the contents of the tube were transferred to 50 ml YM broth in a 500 ml Erlenmeyer flask, and incubated at 28° C. on a rotary shaker at 250 RPM for 18–24 hours. Next, the contents of the flask were transferred to a 2000 ml Fernbach flask containing 700 ml of mineral salt-glucose-NH$_4$Cl medium, of the composition given in Table IX. This was incubated under the same conditions as for the 50 ml flask, but for a total of 40 hours. Next, the entire culture was used to inoculate 20 liters of the same medium contained in a 28 liter New Brunswick fermenter (Model CMF-128S). The initial operating conditions employed were as follows:
Temperature: 29° C.
pH: 6.0
Agitation: 230 rpm
Air Rate: 0.2–0.4 vol/vol/min
Dissolved O$_2$: 90% saturation After an initial growth lag of about 30 hours, cell growth proceeded over the next 30 hours. When the cell concentration reached 0.9 gm/liter, continuous operation was started at an initial dilution rate of 0.07 hr$^{-1}$. Within 48 hours, the cell concentration rose to 2.5 gm/liter. After about 10 culture turnovers, the viscosity and specific productivity started to decline and were eventually almost totally lost. Cell morphology became abnormal and gum quality deteriorated badly. All of these changes proved to be irreversible and the culture did not revert to normal. The results obtained in this run are given in Table X.

TABLE X

| Time Period (Hrs) | Cell Conc'n (gm/l) | Xanthan Conc'n (%) | Viscosity (cp) | Xanthan Volumetric Productivity gm/l/hr) | Xanthan Specific Productivity (gm/gm cells/hr) | Dilution Rate (hr$^{-1}$) | Total Culture Turnovers |
|---|---|---|---|---|---|---|---|
| 0–34 | 1.3–1.9 | .26–.30 | 120–340 | .20 | .11–.15 | .07–.08 | 0–2.5 |
| 34–130 | 2.6–2.56 | .32–.39 | 640–850 | .23–.31 | .10–.13 | .07–.085 | 2.5–9.7 |
| 130–178 | 1.7–2.17 | .23–.265 | 420–430 | .17–.22 | .09–.10 | .07–.08 | 9.7–13.7 |
| 178–202 | 1.0 | .187 | 160 | .13 | .13 | .07 | 13.5–15 |
| 202–266 | .6–1.1 | .12–.14 | 28–48 | .1–.11 | .09–.175 | .077 | 15–20.1 |

EXAMPLE II

*Xanthomonas campestris* XCP-1, ATCC 31600, after isolation as described above, was maintained on EMSY-1 agar slants. These slants were stored at 4° C. and the culture was transferred to fresh slants at bi-weekly intervals.

For inoculum preparation, a loopful of culture from a fresh (<3 day old) slant was inoculated into a 16×125 ml tube containing 7 ml of EMSY-1 broth. The culture was incubated at 28° C. on a rotary shaker at 150 rpm at a 20° C. inclination for 18 hours. At this point, the contents of the tube were transferred to 50 ml of EMS-1 broth (which has the same composition as the EMSY-1 broth except no yeast extract is present) in a 500 ml Erlenmeyer flask, which was incubated at 28° C. on a rotary shaker at 250 rpm for 18 to 24 hours. Next 10 ml volumes of the culture were inoculated into each of two 1000 ml Erlenmeyer flasks containing 100 ml of EMS-1 medium. These were incubated at 28° C. on a rotary shaker at 250 rpm for 18 to 24 hours. The culture contents of both flasks were combined and 150 ml of the culture was used to seed 3000 ml of EMS-3 medium (shown in Table XI) contained in a 7.5 liter fermenter (New Brunswick Model MF-107).

TABLE XI

| Component | Concentration (Per Liter) |
|---|---|
| NH$_4$Cl | 1.28 gm |
| KH$_2$PO$_4$ | 0.66 gm |
| MgSO$_4$.7H$_2$O | 0.41 gm |
| CaCl$_2$.2H$_2$O | 0.04 gm |
| NaCl | 0.026 gm |
| Citric Acid | 0.5 gm |
| FeCl$_3$.6H$_2$O | 15 mg |
| ZnSO$_4$ | 2.5 mg |
| MnSO$_4$ | 0.82 mg |
| CuSO$_4$ | 1.5 mg |
| Na$_2$MoO$_4$ | 0.43 mg |
| H$_3$BO$_3$ | 0.57 mg |
| KI | 0.13 mg |
| Glucose | 22.6 gm |

The fermentation was carried out under the following initial operating conditions:
Temperature: 28° C.
pH: 7.0
Agitation: 300 rpm
Air Rate: 0.5 vol/vol min/min
Dissolved O$_2$: 90% of saturation After 41 hours during which time cell growth proceeded in a batch mode, the agitation rate was increased to 400 rpm and the air rate to 1 vol/vol/min. After an additional 12 hours of growth at which point the cell concentration was about 1.6 gm/liter, continuous operation was started at an initial dilution rate of 0.06 hr$^{-1}$ using the same medium (EMS-3) referred to above. After 15 hours of continuous operation, the agitation rate was increased to 600 rpm due to increasing viscosity in the culture. After correcting a pH upset which caused the pH to rise to 8.0, specific productivity increased from 0.26 to 0.29 gm/gm cells/hour. These results are summarized in Table XII.

TABLE XII

| Time Period (Hrs) | Cell Conc'n (gm/l) | Xanthan Conc'n (%) | Viscosity (cp) | Xanthan Volumetric Productivity gm/l/hr) | Xanthan Specific Productivity (gm/gm cells/hr) | Dilution Rate (hr$^{-1}$) | Total Culture Turnovers |
|---|---|---|---|---|---|---|---|
| 0–36 | 1.58 | 0.56 | 830–940 | 0.41–.42 | .26 | .07–.073 | 0–2.5 |
| | pH reduced from 8 to 6.8 | | | | | | |
| 36–114 | 1.48–1.67 | .52–.65 | 860–1720 | .38–.45 | .23–.29 | .07–.075 | 2.5–8.5 |
| 115–131 | 1.46 | .50 | 1040 | .39 | .27 | .078 | 8.5–9.6 |
| 132–160 | .48–1.17 | .18–.47 | 120–550 | .13–.38 | .27–.33 | .07–.073 | 9.6–11.7 |
| | cell concentration decreased | | | | | | |
| 160–188 | batch growth | | | | | | |
| 188–206 | 1.09–1.26 | .47–.49 | 410–870 | .24–.29 | .19–.27 | .05–.06 | 11.7–12.2 |
| 206–233 | batch growth | | | | | | |
| 233–325 | 1.69–1.86 | .68–.80 | 1780–2310 | .30–.42 | .18–.25 | .04–.055 | 12.2–16.8 |
| 325–379 | 1.55–1.71 | .53–.64 | 900–1440 | .38–.46 | .25–.27 | .07–.073 | 16.8–20.7 |
| 397–398 | dilution rate upset | | | | | | |
| 398–517 | 1.67–1.97 | .44–.53 | 500–870 | .32–.38 | .18–.20 | .073–.075 | 20.7–30.4 |

At 5.5 culture turnovers, the specific productivity started to decline to 0.24–0.26 due to an increase in dilution rate and temperature and pH cycling. After two periods of batch growth made in attempts to bring the cell concentration back to normal, the culture was maintained at a specific productivity of 0.2 gm/gm cells per hour, which was still higher than that exhibited by the parent strain (B-1459). Specific productivity then improved to 0.22–0.23 gm/gm cells per hour at a dilution rate of 0.05 hr$^{-1}$, and increased again to 0.26–0.27 when the dilution rate was increased to 0.07 hr$^{-1}$. At 395 hours, the specific productivity slowly declined to 0.18–0.19 gm/gm cells per hour, which was maintained until 517 hours. Thus, *Xanthomonas campestris* XCP-1 ATCC 31600, was grown continuously for a period of 30 culture turnovers at specific productivities of 0.18–0.19 up to 0.29 gm/gm cells/hour which is 1.5 to 2.4 times higher than the specific productivity of *Xanthomonas campestris* NRRL B-1459, and culture degeneration of any consequence was avoided.

EXAMPLE III

In this example, an inoculum of *Xanthomonas campestris* XCP-1, ATCC 31600, was prepared in accordance with the procedure outlined in Example II except that the 50 ml and 100 ml cultures were grown in EMS-2 medium (shown in Table VII) which contained 0.04 gm/liter of yeast extract. After 24 hours of batch growth, the cell concentration was about 1.5 gm/liter and continuous operation was started at a dilution rate of 0.059 hr$^{-1}$. The agitation rate was increased at this point to 800 rpm.

The results of this run are given below in Table XIII.

TABLE XIII

| Time Period (Hrs) | Cell Conc'n (gm/l) | Xanthan Conc'n (%) | Viscosity (cp) | Xanthan Volumetric Productivity gm/l/hr) | Xanthan Specific Productivity (gm/gm cells/hr) | Dilution Rate (hr$^{-1}$) | Total Culture Turnovers |
|---|---|---|---|---|---|---|---|
| 0–21 | 1.9–2.2 | .8–.89 | 2450 | .47–.475 | .22–.24 | .059 | 0–0.8 |
| 21–95 | 1.75–2.0 | .57–.66 | 1280–1720 | .48–.55 | .25–.30 | .08–.088 | 0.8–5.8 |
| 95–265 | 2.1–2.35 | .61–.72 | 1418–1750 | .49–.58 | .22–.25 | .076–.084 | 19.2–28.4 |

The data show that *Xanthomonas campestris* XCP-1 ATCC 31600 was grown for 19 culture turnovers at a high specific productivity ranging from 0.22 to 0.30 gm xanthan/gm cells/hr. Only after 265 hours of continuous operation when the unit became contaminated with an unknown bacterium did the specific productivity decrease, ranging from 0.16 to 0.25 which is still substantially higher than the specific productivity of the parent strain B-1459. Thus, it is seen that *Xanthomonas campestris* XCP-1 ATCC 31600 can also be grown in a minimal medium supplemented with 0.04% yeast extract. Actually, any amount of yeast extract or yeast autolysate ranging from 0.005% to 0.1% can be used although 0.02% to 0.04% is optimal when balancing utility and cost considerations.

We claim:

1. A method for the production of a heteropolysaccharide which comprises continuously culturing a degenerative resistant strain of bacteria designated *Xanthomonas campestris* XCP-1, having the identifying characteristics of ATCC 31600, in an aqueous medium comprising the assimilable sources of carbon, nitrogen and inorganic substances wherein said medium is continuously fed to a fermentation zone to produce said polysaccharide, and withdrawing the resulting fermented medium from said zone.

2. The method of claim 1 in which said medium is a minimal medium.

3. The method of claim 2 wherein said minimal medium also contains as a complex nitrogen source, one of the group consisting of yeast extract and yeast autolysate.

4. The method of claim 1 in which the fermentation is conducted at a specific xanthan productivity in excess of 0.2 gm xanthan/gm cells/hr.

5. The method of claim 1 wherein said fermented medium is withdrawn from said zone at a rate such that an essentially steady state condition is maintained in said zone.

6. A method for the production of a heteropolysaccharide which comprises continuously culturing a degenerative resistant strain of *Xanthomonas campestris* P-1 having the identifying characteristics of ATCC 31600 in a minimal medium containing a growth limiting nutrient and wherein said medium is continuously fed to a first fermentation zone to produce additional amounts of said strain together with said heteropolysaccharide, thereafter transferring the effluent from said first zone to a second fermentation zone, and adding a fermentable sugar to said effluent in said second zone whereby the formation of heteropolysaccharide in said second zone is maximized.

7. The method of claim 6 in which the fermentable sugar employed in glucose.

8. The method of claims 1 or 6 in which the heteropolysaccharide is xanthan.

9. The biologically pure culture of a novel strain of *Xanthomonas campestris* XCP-1, having the identifying characteristics of ATCC 31600, said strain being capable of producing xanthan gum in recoverable amounts upon fermentation of an aqueous nutrient medium containing assimilable sources of carbon, nitrogen and inorganic substances and being resistant to cell degeneration when subjected to continuous fermentation conditions.

10. A biologically pure culture consisting essentially of *Xanthomonas campestris* XCP-1 ATTC 31600.

11. A biologically pure culture consisting essentially of *Xanthomonas campestris* XCP-1 ATTC 31600, said culture being degenerative resistant when continuously cultured in an aqueous nutrient medium, and capable of producing xanthan gum in good yields.

12. A bacterial culture consisting essentially of *Xanthomonas campestris* XCP-1 ATTC 31600.

13. A bacterial culture consisting essentially of *Xanthomonas campestris* XCP-1 ATTC 31600, said culture being degenerative resistant when continuously cultured in an aqueous nutrient medium, and capable of producing xanthan gum in good yields.

14. A bacterial culture consisting essentially of *Xanthomonas campestris* XCP-1 ATTC 31600, said culture capable of producing xanthan gum in recoverable amounts upon fermentation of an aqueous nutrient medium containing assimilable sources of carbon, nitrogen, and inorganic substances.

* * * * *

UNITED STATES PATENT OFFICE
CERTIFICATE OF CORRECTION

PATENT NO. : 4,407,951

DATED : October 4, 1983

INVENTOR(S) : William P. Weisrock and Edward F. McCarthy

It is certified that error appears in the above-identified patent and that said Letters Patent are hereby corrected as shown below:

Columns 9 and 10, next to last line of Table XII (first column), "397-398" should be --379-398--;

Column 12, line 26, "in" should be --is--.

Signed and Sealed this

Sixteenth Day of April 1985

[SEAL]

Attest:

DONALD J. QUIGG

Attesting Officer

Acting Commissioner of Patents and Trademarks